United States Patent [19]
Park et al.

[11] Patent Number: 5,707,927
[45] Date of Patent: Jan. 13, 1998

[54] CULTIVATING METHOD FOR BEAN SPROUT AND GREEN BEAN SPROUT USING CINNAMIC ACID DERIVATIVES

[75] Inventors: Kyong Pae Park; Changsok Oh; Inwoo Yi, all of Seoul, Rep. of Korea

[73] Assignee: Korea Institute of Science and Technology, Seoul, Rep. of Korea

[21] Appl. No.: 711,227

[22] Filed: Sep. 9, 1996

[30] Foreign Application Priority Data

Sep. 12, 1995 [KR] Rep. of Korea .................. 29641-1995

[51] Int. Cl.$^6$ .................................................. A01N 37/10
[52] U.S. Cl. .................................. 504/136; 504/321
[58] Field of Search ....................... 504/321, 136

[56] References Cited

FOREIGN PATENT DOCUMENTS

| | | |
|---|---|---|
| 81-1405 | 10/1981 | Rep. of Korea . |
| 81-1406 | 10/1981 | Rep. of Korea . |
| 89-4625 | 11/1989 | Rep. of Korea . |
| 93-1374 | 2/1993 | Rep. of Korea . |

OTHER PUBLICATIONS

Ting, I. P. *Plant Physiology*. Addison–Wesley Pub. Co. 1982. pp. 502–503.

Demos et al. "The effects of ten phenolic compounds on hypocotyl growth and mitochondrial metabolism of mung bean." *Am. J. Bot.* 62(1):97–102. 1975.

John R. Johnson, "The Perkin Reaction and Related Reactions", *Organic Reactions*, 5th ed. (John Wiley & Sons, Inc., 1954), pp. 211, 248–249.

Gary J. Loake et al., "Phenylpropanoid Pathway Intermediates Regulate Transient Expression of a Chalcone Synthase Gene Promoter," *The Plant Cell*, No. 3 (Aug. 1991), pp. 829–840.

David A. Morris et al., "Invertase and Auxin–induced Elongation in Internodal Segments of *Phaseolus vulgaris*," *Phytochemistry*, vol. 23, No. 10 (1984), pp. 2163–2167.

Richard A. Dixon, "The Phytoalexin Response: Elicitation, Signalling and Control of Host Gene Expression", *Biol. Rev.*, (1986) 61, pp. 239–291.

*Primary Examiner*—S. Mark Clardy
*Attorney, Agent, or Firm*—Darby & Darby

[57] ABSTRACT

A cultivating method for bean sprouts and green bean sprouts uses a compound represented by formula (1) or a compound represented formula (1) with a benzy adenine as a disinfectant, and the beans are soaked in water in which the disinfectant is dissolved, or the soaked beans are sprayed with the water;

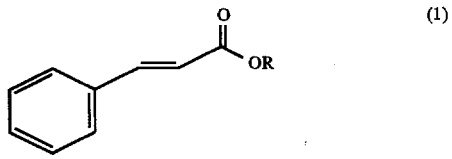

wherein, R represents hydrogen, sodium, potassium, methyl or ethyl.

The cultivating method prevents rotting without growth inhibition.

5 Claims, No Drawings

CULTIVATING METHOD FOR BEAN SPROUT AND GREEN BEAN SPROUT USING CINNAMIC ACID DERIVATIVES

BACKGROUND OF THE INVENTION

1. Field of the Invention

The present invention relates to a cultivating method for bean sprouts and green bean sprouts which is capable of cultivating bean sprouts and green bean sprouts more sanitarily and safely to men by using a disinfectant composition containing a cinnamic acid or a cinnamate and a cinnamic ester (hereinafter, called a cinnamic group) represented by the following structural formula (1).

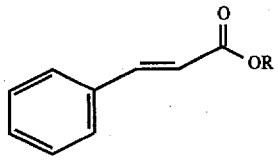

(1)

R = H, Na, K, $CH_3$, $C_2H_5$

2. Description of the Conventional Art

A bean sprout or a green bean sprout is an important native food of Asia. These sprouts are apt to be infected by mold or bacteria and become rotten because they are cultivated underwater under conditions of darkness.

To solve such a problem, cultivators of bean sprouts sometimes used to cultivate bean sprouts by using unapproved harmful agricultural chemicals. Since bean sprouts and green bean sprouts have a short cultivation and distribution period, in case an agricultural chemical is used, the rotting of the bean sprouts can be prevented, but the poison residue may remain in the bean sprouts which can cause a serious problem.

As a solution to these problems, a cultivating method for a bean sprout using a disinfectant less harmful and poisonous to men was disclosed in Korean Patent Publication No. 89-4625. The method is an excellent one, but a disinfectant requiring a relatively high concentration (1.5~5 g per 70 Kg beans) is used.

Another solution is the cultivating of bean sprouts using a lower concentration of a disinfectant (0.4~0.5 g per 70 Kg beans) harmless to men and having a sufficient disinfection effect as disclosed in Korean Patent Publication No.93-1374). This is also an excellent method, but since the disinfectant is not a natural substance, it is not desirable to be generally used.

SUMMARY OF THE INVENTION

Accordingly, it is an object of the present invention to provide a cultivating method for bean sprouts and green bean sprouts which uses a chemical compound having a concentration of 0.2~5.0 g per 70 Kg of beans and a sufficient disinfection effect, and which is harmless to humans and which can be found existing as a natural substance.

DETAILED DESCRIPTION OF THE PRESENT INVENTION

The present invention will now be described in detail with reference to the accompanying examples.

Cinnamic acid and cinnamaldehyde are chief ingredients of cinnamon bark which is a natural spice existing in nature, and have long been used in Eastern and Western cultures without any problem in their usage.

A main defensive reaction against mold infection of plants belonging to the bean family is a rapid accumulation of isoflavonoid phytoalexin which is an antibiotic, on infected portions.(R. A. Dixon; Biol. Rev.;1986,61,239–291). Here, genes of a chalcone synthetase and a phenylalanine ammonia lyase are enzymes related to a phytoalexin biosynthesis. (G. J. Loake; A. D. Choudhary; M. J. Harrison; M. Mavandad; C. J. Lamb; R. A. Dixon; The Plant Cell; 1991,3, 829–840). When a cinnamic acid, an intermediate of Phenylpropanoid generated by the reaction of both L-phenylalanine and phenylalanine ammonia lyase, is treated in a low concentration, a revelation of the above-mentioned enzyme is stimulated, but when the cinnamic acid is treated in a high concentration, a revelation of the enzyme is inhibited. (G. J. Loake; A. D. Choudhary; M. J. Harrison; M. Mavandad; C. J. Lamb; R. A. Dixon; The plant Cell; 1991,3,829–840). In addition, a cinnamic acid is one of the products generated in the above course and is known to always exist in the plants belonging to the bean family.

In the course of examining the disinfection effect on bean sprouts of the cinnam anilede disclosed in Korean Patent Publication 93-1374, it was found out that the cinnam anilide was changed into a cinnamic acid. On the basis of this material, five cinnamic acids such as a cinnamic acid, a cinnamic acid sodium salt, a cinnamic acid potassic salt, a cinnamic acid methyl ester and a cinnamic acid ethyl ester were prepared, and to determine the disinfection effect of these compounds, bean sprouts were cultivated by using the above-mentioned compounds and then their disinfection effects were compared and examined. Commercially available cinnamic acid was used or cinnamic acid was prepared according to a known method for this experiment(Adams; "Organic reaction" Coll Vol 1, p.251, John Wiley and Sons, New York, 1942). The cinnamate used was prepared by the reaction of the cinnamic acid and sodium carbonate or potassium carbonate. And for preparing the cinnamic acid methyl ester and ethyl ester used in the experiment, cinnamic acid and alcohol were reacted in an acid catalyst.

The above-mentioned cinnamic acid group is a safe compound which is listed as an approved food additive in the notification from the Korean Ministry of Health and Social Affairs, and especially, the cinnamic acid is a natural substance biosynthesized in plants belonging to the bean family. A cinnamic acid ester is absorbed in the bean sprout and decomposed and finally is changed into a cinnamic acid, and the salt of the cinnamic acid is easily dissolved in water and so is easy to treat. So far, such materials have been synthesized chemically or their reactivity to the enzyme has been studied from a biochemical viewpoint, but they have not been used as a disinfectant.

To demonstrate the disinfection effect of the cinnamic acid group, experiments were conducted in three factories. The following Table 1 shows the amount of each chemical needed for 1 kg of dry beans to absorb the chemical having a 0.75~15 ppm concentration into the beans during the initial process of soaking the beans in water. The chemical having a 0.75~15 ppm concentration absorbed in the bean is gradually reduced in the concentration during the growth of the bean sprouts to have 0.1~2.0 ppm of cinnamic acid remaining in the last step of cultivating the bean sprouts. Here, although the initially absorbed chemicals were, respectively, different, the final remaining material was a cinnamic acid.

TABLE 1

| chemical dosage for absorbing 0.75–15 ppm | |
| --- | --- |
| kinds of chemicals | dosage of chemicals |
| cinnamic acid | 3–60 |
| cinnamic acid sodium salt | 4–75 |
| cinnamic acid potassium salt | 4–75 |
| cinnamic acid methyl ester | 2.5–50 |
| cinnamic acid ethyl ester | 2.5–50 |

*The unit of the dosage of chemicals is mg/kg dry beans

While a cis-trans isomerism occurs on a cinnamic acid, an auxin action which hastens the growth is inter-competitively inhibited, which causes a growth inhibiting action in the growth of bean sprouts (Morris, K. A.; Arthur, E. D. Phytochemistry 1984, 23, 2163), but when using the above concentration of chemicals, no growth inhibiting action was observed.

When the concentration of the cinnamic acid group is raised, the growth inhibiting action appears, and since the cultivators of bean sprouts may tend to use a larger amount of chemicals than the specified amount, the expected effect due to the growth inhibition should be considered.

To overcome such a problem, a variety of growth controllers have been adopted, and as a result, an N-benzyl adenine is used as a supplement. That is, by using this chemical, fine roots are not generated, and soft and plumpy roots can be obtained( Korean Patent Publication 81-1405, 81-1406, 93-1374).

The present inventors examined the concentration range of the cinnamic group having a disinfection effect with no growth inhibiting action for five kinds of cinnamic acid groups. The proper amounts of the cinnamic acid group to use in the initial process of soaking beans in water, is shown in Tables 3 and 4 for examples 3 and 4. As a result, it was found that regardless of the kind of cinnamic acid, the preferred amount of the chemicals absorbed was 0.75–15ppm per each weight of beans. Taking the cinnamic acid for example, the disinfection effect was weak when 3 mg of chemical was absorbed in 1 kg of dry beans, but when 100 mg of chemical was absorbed, the growth inhibiting action began to be stronger, and when 200 mg of chemical was absorbed, it proved unusable due to the occurrence of a serious growth inhibiting action.

Second, the inventors checked the range of the dosage of a cinnamic acid group mixed with an N-benzyl adenine which has a disinfection effect and which shows no sign of growth inhibition. The dosage of the N-benzyl adenine used was 4–11 mg (Korean Patent Publication 93-1374), and the concentration range of the cinnamic acid group corresponding to that dosage is shown in Table 2. Taking the cinnamic acid for example, even when 3 mg of cinnamic acid was used, a disinfection effect appeared. The optimum concentration was 5–30 mg of cinnamic acid and 4–11 mg of benzyl adenine per 1 kg of dry beans, but even when 150 mg of cinnamic acid was used, it caused no growth inhibition.

TABLE 2

| the concentration range of a cinnamic acid group for 4–11 mg benzyl-adenine | |
| --- | --- |
| kinds of chemicals | dosage of chemicals |
| cinnamic acid | 3–150 |
| cinnamic acid sodium salt | 4–200 |
| cinnamic acid potassium salt | 4–200 |

TABLE 2-continued

| the concentration range of a cinnamic acid group for 4–11 mg benzyl-adenine | |
| --- | --- |
| kinds of chemicals | dosage of chemicals |
| cinnamic acid methyl ester | 2.5–125 |
| cinnamic acid ethyl ester | 2.5–125 |

*The unit of the dosage of chemicals is mg/kg dry bean

Regarding the preparation method of the chemicals, in case only a cinnamic acid group is used, 3–60 mg of cinnamic acid (the amount needed in 1 kg dry beans) is mixed with an interfacial active agent such as a sodium carboxy methyl cellulose (hereinafter, called NaCMC) to make an aqueous solution, and the cinnamic acid is dissolved in an aqueous solution containing $NA_2CO_3$ or $K_2CO_3$. On the other hand, as in the example, when a suitable amount of a cinnamic acid ester is mixed with an interfacial active agent such as NaCMC, the chemical can be easily dissolved in water. When the cinnamic acid group is mixed with the benzyl adenine, the cinnamic acid group and the benzyl adenine are mixed with NaCMC to make an aqueous solution, and when only the cinnamic acid is used, the cinnamic acid and the benzyl adenine are dissolved in an ethyl alcohol to be used as the treating chemical.

Bean sprouts as a crop are produced all year and cultivated to proper size according to the temperature, water temperature or some other necessities, and the period during which there can occur some problem is the dry period in a late spring. Therefore, experiments were intensively conducted from early May to mid June. A three-kwan container (that is, 3×3.75 Kg=11.25 Kg) was used for cultivating bean sprouts. A plurality of holes were bored in the bottom of the plastic container to allow water to drain freely. Each step of the cultivating method of the bean sprouts will now be described.

Soaking beans in the water: 1.5 Kg of dry beans were put in the above-mentioned container, and sufficient water was supplied thereto every three hours. Then the beans were left for 24 hours to double in weight. The chemical prepared as above was diluted in 3L water to be used in this course. Although the water amount is small, the water draining through the holes in the bottom of the container is caught and sprayed again on the beans to maximize the absorption effect.

Putting the beans in another container for cultivation: The beans after being soaked in water were transferred to a different container for cultivating into bean sprouts. Here, the chemical prepared as above process was diluted in water as above to spray on the beans.

Cultivating the bean sprouts: To cultivate the bean sprouts, first, light was shut out by using a thick cloth so as not to let in light. Bean sprouts were cultivated until the size of the bean sprouts became about 11 cm, and the weight reached about 9.0 Kg of bean sprouts from an initial 1.5 Kg of dry beans. For six to seven days, water as needed was sprayed on the 1.5 Kg of dry beans at a proper time to cultivate them to the point corresponding to the object of the experiment, and then the results were compared and checked.

Some examples of cultivating method according to the present invention will now be described in detail.

EXAMPLE 1

(preparation of the Chemicals)

Case 1. 14.8 mg of cinnamic acid and 45 mg of NaCMC were dissolved in 1 ml of water. The resultant chemical was dosed on 1 Kg of dry beans.

Case 2. 14.5 mg of cinnamic acid and 10.6 mg of $Na_2CO_3$ were dissolved in 1 ml of water. The resultant chemical was dosed on 1 Kg of dry beans.

Case 3. 14.5 mg of cinnamic acid and 13.8 mg of $K_2CO_3$ were dissolved in 1 ml of water. The resultant chemical was dosed on 1 Kg of dry beans.

Case 4. 16.2 mg of cinnamic acid methyl ester and 45 mg of NaCMC were dissolved in 1 ml of water. The resultant chemical was dosed on 1 Kg of dry beans.

Case 5. 17.6 mg of cinnamic acid ethyl ester and 45 mg of NaCMC were dissolved in 1 ml of water. The resultant chemical was dosed on 1 Kg of dry beans.

Case 6. 14.8 mg of cinnamic acid and 5 mg of benzyl adenine were dissolved in 1 ml of ethyl alcohol. The resultant chemical was dosed on 1 Kg of dry beans.

Case 7. 17.0 mg of cinnamic acid sodium salt, 5 mg of benzyl adenine and 45 mg of NaCMC were dissolved in 1 ml of water. The resultant chemical was dosed on 1 Kg of dry beans.

Case 8. 18.6 mg of cinnamic acid potassium salt, 5 mg of benzyl adenine and 45 mg of NaCMC were dissolved in 1 ml of water. The resultant chemical was dosed on 1 Kg of dry beans.

Case 9. 16.2 mg of cinnamic acid methyl ester, 5 mg of benzyl adenine and 45 mg of NaCMC were dissolved in 1 ml of water. The resultant chemical was dosed 1 Kg of dry beans.

Case 10. 17.6 mg of cinnamic acid ethyl ester, 5 mg of benzyl adenine and 45 mg of NaCMC were dissolved in 1 ml of water. The resultant chemical was dosed on 1 Kg of dry beans.

EXAMPLE 2

Soaking the beans in the water: 1.5 Kg of dry beans were put in the container, and every three hours, sufficient water was supplied thereto. Then the beans were left for 24 hours to double in weight. Then the chemical dosage was carried out, wherein the prepared chemical was diluted in 3L water to be sprayed on the beans.

Cultivating bean sprouts in another container: The beans soaked in water as above were transferred to a different container for cultivating bean sprouts. Then light was shut out by using a thick cloth so as not to let in light. Bean sprouts were cultivated for six to seven days until the size of the bean sprouts became about 11 cm, and the weight reached about 9.0 Kg of bean sprouts from an initial 1.5 Kg of dry beans.

EXAMPLE 3

By varying the dosage of the chemicals prepared in cased 1 through 5 of the example 1 to 1 Kg of dry beans, and carrying out the procedure of example 2, the disinfection effect[*1] of the chemicals were examined, and the results are shown in Table 3.

TABLE 3

| | Disinfection Effect according to the Dosage | | | | |
|---|---|---|---|---|---|
| | dosage of chemicals(ml/Kg) | | | | |
| kinds of chemical | 0.0 | 0.13 | 0.25 | 0.50 | 1.0 |
| case 1 in example 1 | − | − | + | ++ | ++ |
| case 2 in example 1 | − | − | + | ++ | ++ |

TABLE 3-continued

| | Disinfection Effect according to the Dosage | | | | |
|---|---|---|---|---|---|
| | dosage of chemicals(ml/Kg) | | | | |
| kinds of chemical | 0.0 | 0.13 | 0.25 | 0.50 | 1.0 |
| case 3 in example 1 | − | − | + | ++ | ++ |
| case 4 in example 1 | − | − | ++ | ++ | ++ |
| case 5 in example 1 | − | − | ++ | ++ | ++ |

*1: (−) represents a degree of a lusterless or rotten bean sprout, (+) means a degree of the contrary case and (++) represents a high degree of the contrary case.

EXAMPLE 4

By varying the dosage of the chemicals prepared in cases 1 through 5 of the example 1 to 1 Kg of dry beans, and carrying out the procedure of example 2, the growth inhibition[2] of the chemicals was examined, and the results are shown in Table 4.

TABLE 4

| | Growth Inhibition according to the Dosage | | | | | |
|---|---|---|---|---|---|---|
| | dosage of chemicals (ml/kg) | | | | | |
| kinds of chemical | 4.0 | 5.0 | 6.0 | 7.0 | 8.0 | 9.0 |
| case 1 in example 1 | ++ | ++ | ++ | +− | − | − |
| case 2 in example 1 | ++ | ++ | ++ | ++ | ++ | +− |
| case 3 in example 1 | ++ | ++ | ++ | ++ | ++ | +− |
| case 4 in example 1 | ++ | ++ | +− | +− | − | − |
| case 5 in example 1 | ++ | ++ | +− | +− | − | − |

*2:(−) represents poor growth or the appearance of fine roots in the bean sprouts, (+) means the effect of the contrary case and the strong effect of the contrary case.

EXAMPLE 5

The procedure of example 2 was also carried out and after treating the resultant materials with the chemicals prepared in cases 1 through 5 of the example 1 or with benzyl adenine (5 mg), the bean sprouts were cultivated for seven days and then the resultant weights were measured, which are shown in Table 5.

TABLE 5

| The weight of bean sprouts after the chemical treatment | |
|---|---|
| dosed chemical | weight of bean sprouts |
| case 1 in example 1 | 8.46 |
| case 2 in example 1 | 8.47 |
| case 3 in example 1 | 8.44 |
| case 4 in example 1 | 8.47 |
| case 5 in example 1 | 8.46 |
| benzyl adenine | 8.45 |
| no treatment | 8.50 |

EXAMPLE 6

By varying the dosage of the chemicals prepared in cases 6 through 10 of example 1 to 1 Kg of dry beans, and carrying out the procedure of example 2, the disinfection effect[*1] of the chemicals was examined, and the results are shown in Table 6.

TABLE 6

Disinfection Effect according to the Dosage

| kinds of chemical | dosage of chemicals(ml/Kg) | | | | |
|---|---|---|---|---|---|
| | 0.0 | 0.13 | 0.25 | 0.50 | 1.0 |
| case 6 in example 1 | − | − | + | ++ | ++ |
| case 7 in example 1 | − | − | + | ++ | ++ |
| case 8 in example 1 | − | − | + | ++ | ++ |
| case 9 in example 1 | − | − | ++ | ++ | ++ |
| case 10 in example 1 | − | −+ | ++ | ++ | ++ |

EXAMPLE 7

By varying the dosage of the chemicals prepared in cases 6 through 10 of the example 1 to 1 Kg of dry beans, and carrying out the procedure of example 2, the growth inhibition*² of the chemicals was examined, and the results are shown in Table 7.

TABLE 7

Growth Inhibition according to the Dosage

| kinds of chemicals | dosage of chemicals | | | | | | |
|---|---|---|---|---|---|---|---|
| | 6 | 8 | 10 | 12 | 14 | 16 | 18 |
| case 6 in example 1 | ++ | ++ | ++ | ++ | +− | — | — |
| case 7 in example 1 | ++ | ++ | ++ | ++ | ++ | ++ | +− |
| case 8 in example 1 | ++ | ++ | ++ | ++ | ++ | ++ | +− |
| case 9 in example 1 | ++ | ++ | ++ | +− | — | — | — |
| case 0 in example 1 | ++ | ++ | +− | — | — | — | — |

EXAMPLE 8

The procedure of example 2 was also carried out and after treating the resultant materials with the chemicals prepared in cases 6 through 10 of the example 1, respectively, the bean sprouts were cultivated for seven days and then the resultant weights were measured, which are shown in Table 8.

TABLE 8

The weight of bean sprouts after the chemical treatment

| dosed chemical | weight of bean sprouts |
|---|---|
| case 6 in example 1 | 9.44 |
| case 7 in example 1 | 9.43 |
| case 8 in example 1 | 9.43 |
| case 9 in example 1 | 9.44 |
| case 10 in example 1 | 9.43 |
| benzyl adenine (5 mg) | 9.45 |
| no treatment | 8.50 |

Although the preferred examples of the present invention have been disclosed for illustrative purposes, those skilled in the art will appreciate that various modifications, additions and substitutions are possible, without departing from the scope and spirit of the invention as recited in the accompanying claims.

What is claimed:

1. A method for cultivating bean and green bean sprouts comprising:

applying a disinfectant to a bean, a green bean, a bean sprout or a green bean sprout;

said disinfectant comprising a compound of formula (1) or a mixture of the compound of formula (1) and a benzyl adenine;

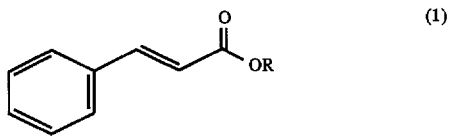

wherein R represents hydrogen, sodium, potassium, methyl or ethyl.

2. The cultivating method of claim 1, wherein beans or green beans are soaked in water in which the disinfectant is dissolved, or the soaked beans or green beans are sprayed with the water in which the disinfectant is dissolved.

3. The cultivating method of claim 1, wherein the disinfectant is used in the amount of 2.5~200 mg per 1 Kg of dry beans.

4. The cultivating method of claim 1, wherein the disinfectant comprising 2.5~200 mg of the compound of formula (1) 4~11 mg of benzyl adenine is used per 1 Kg of dry beans.

5. A method for disinfecting bean and green bean sprouts comprising:

applying a disinfectant to a bean, a green bean, a bean sprout or a green bean sprout;

said disinfectant comprising a compound of formula (1) or a mixture of the compound of formula (1) and a benzyl adenine;

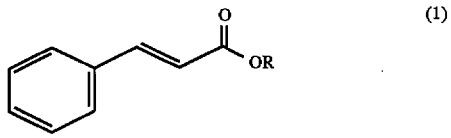

wherein R represents hydrogen, sodium, potassium, methyl or ethyl.

* * * * *